US006998486B2

(12) United States Patent
Shibuya et al.

(10) Patent No.: US 6,998,486 B2
(45) Date of Patent: Feb. 14, 2006

(54) PROCESS FOR PRODUCTION OF CYCLIC DIAMINE COMPOUNDS OR SALTS THEREOF

(75) Inventors: Kimiyuki Shibuya, Saitama (JP); Tadaaki Ohgiya, Saitama (JP); Yukihiro Sato, Tokyo (JP); Toru Miura, Tokyo (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 10/498,984

(22) PCT Filed: Dec. 27, 2002

(86) PCT No.: PCT/JP02/13793

§ 371 (c)(1),
(2), (4) Date: Jun. 25, 2004

(87) PCT Pub. No.: WO03/057675

PCT Pub. Date: Jul. 17, 2003

(65) Prior Publication Data

US 2005/0032814 A1    Feb. 10, 2005

(30) Foreign Application Priority Data

Dec. 28, 2001    (JP)    ............................. 2001-401044

(51) Int. Cl.
   *C07D 235/28*    (2006.01)
(52) U.S. Cl. .................................................... 544/368
(58) Field of Classification Search ................. 544/368
   See application file for complete search history.

(56) References Cited

U.S. PATENT DOCUMENTS

| 2004/0038987 A1 | 2/2004 | Shibuya et al. |
| 2004/0176593 A1 | 9/2004 | Shibuya et al. |
| 2005/0032814 A1 | 2/2005 | Shibuya et al. |

FOREIGN PATENT DOCUMENTS

| EP | 334 818 | 9/1989 |
| EP | 335 586 | 10/1989 |
| WO | 95/34304 | 12/1995 |
| WO | 98/54153 | 12/1998 |
| WO | 01/00588 | 1/2001 |
| WO | 01/04110 | 1/2001 |

OTHER PUBLICATIONS

Rashmi Rastogi, et al, "Synthesis of 2-substituted thiobenzimidazoles as potential anthelminthics", Archiv der Pharmazie, vol. 316, No. 7, pp. 638-643 1983.
U.S. Appl. No. 10/498,984, filed Jun. 25, 2004, Shibuya, et al.
U.S. Appl. No. 10/883,710, filed Jul. 6, 2004, Shibuya, et al.
U.S. Appl. No. 10/763,241, filed Jan. 26, 2004, Shibuya, et al.
U.S. Appl. No. 10/535,705, filed May 20, 2005, Shibuya, et al.

*Primary Examiner*—Kamal A. Saeed
(74) *Attorney, Agent, or Firm*—Oblon, Spivak, McClelland, Maier & Neustadt, P.C.

(57) ABSTRACT

The present invention is directed to a process for producing cyclic diamine compounds (4) or salts or intermediates thereof according to the following reaction scheme:

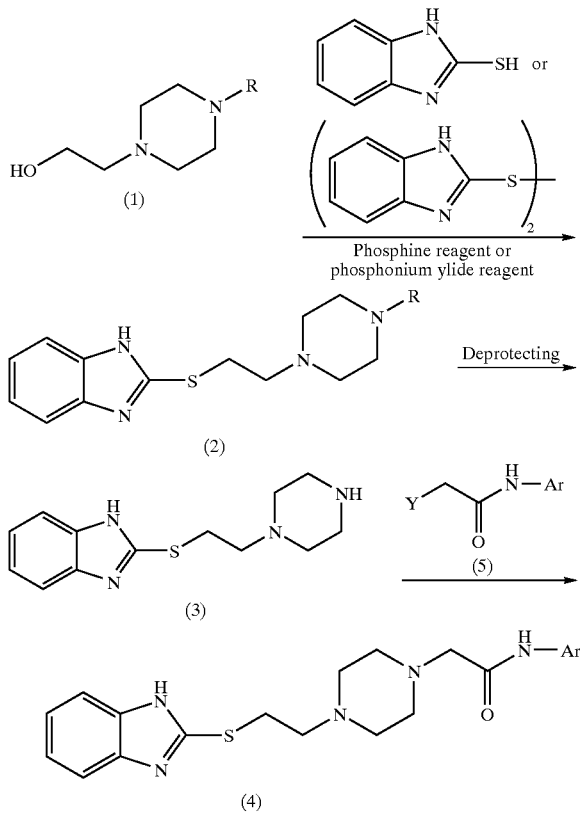

(wherein R is a protective group and Ar is an optionally substituted aryl group).

According to the present invention, the cyclic diamine compounds (4) useful as drugs or salts or intermediates thereof can be produced at high levels of yield and purity in terms of industrially advantageous productivity.

6 Claims, No Drawings

PROCESS FOR PRODUCTION OF CYCLIC DIAMINE COMPOUNDS OR SALTS THEREOF

TECHNICAL FIELD

The present invention relates to a process for production of cyclic diamine compounds or salts thereof serving as an ACAT inhibitor, as well as intermediates thereof.

BACKGROUND ART

Acyl-Coenzyme A cholesterol acyltransferase (ACAT) is an enzyme that is capable of catalyzing synthesis of a cholesterol ester from cholesterol and plays an important role in the metabolism and absorption of cholesterol in the gastrointestinal tract.

In recent years, it has been reported that the plasma cholesterol level can be effectively suppressed by controlling the activity of ACAT present in the small intestine and the liver. So far, a number of studies have been carried out for ACAT inhibitors.

Meanwhile, the present inventors focused on ACAT in vascular wall and studied on the selective inhibitors against this type of ACAT. As a result, it was found that among azole compounds having a cyclic diamine structure, cyclic diamine compounds represented by the following formula (4):

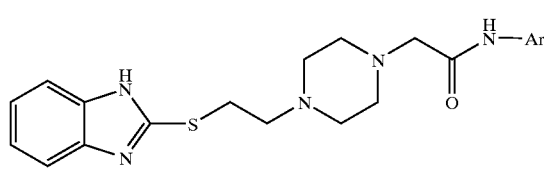

(4)

(wherein Ar represents an aryl group which may have a substituent(s)) were useful as therapeutic drugs for hyperlipidemia and arteriosclerosis, having less side effect and excellent oral absorption property. Based on such findings, the present inventors filed an international patent application (WO 98/54153).

In the above patent application, the compound (4) can be produced through the 5-step process of reactions as described below:

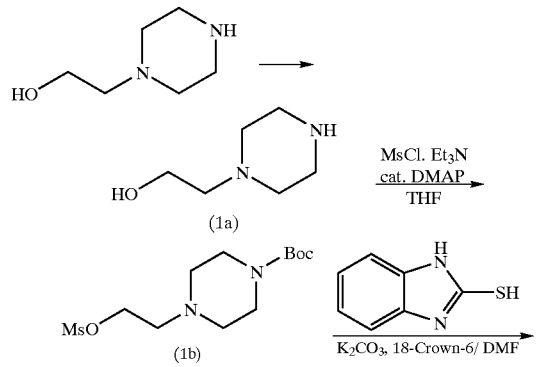

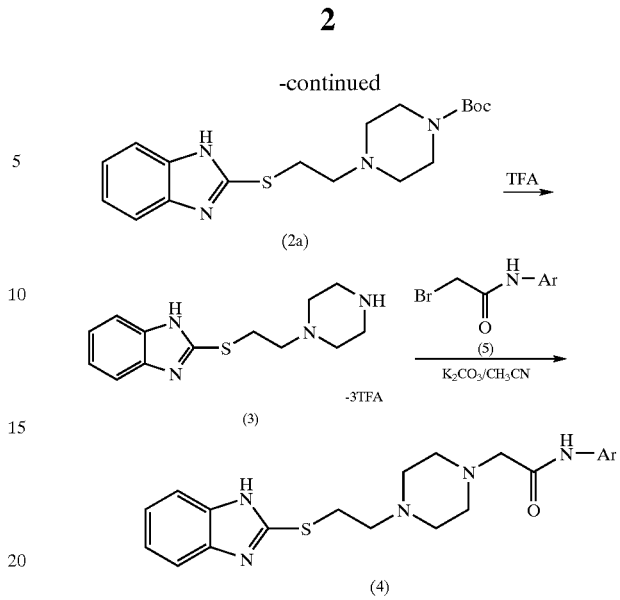

(wherein Ar has the same meaning as defined above).

According to this reaction process, transformation of alcohol of the compound (1a) having an amino group protected by a tert-butoxy carbonyl group (Boc) into thioether is performed by a method in which the hydroxyl group is transformed to a methanesulfonyloxy group which readily leaves, followed by reacting with 2-mercaptobenzimidazole in the presence of a base. However, since the compound (1b) having such a leaving group has poor stability, by-products and decomposed products from the compound (1b) are readily generated during removal of the solvent included in post treatment of a large scale synthesis. As a result, it is difficult to avoid problems such as requirement of cumbersome purification procedures and variation in yield.

An object of the present invention is to provide an industrially advantageous process for producing a compound (4) serving as an ACAT inhibitor or a salt thereof. Another object of the invention is to provide a process for producing an intermediate therefor or a salt thereof.

DISCLOSURE OF THE INVENTION

In view of the foregoing, the present inventors have carried out extensive studies, and have found that a compound (4) or a salt thereof can be effectively and shortly produced at high levels of yield and purity when the reaction was carried out using a phosphine reagent or a phosphonium ylide reagent needed to transform alcohol into thioether, as shown in the reaction scheme below:

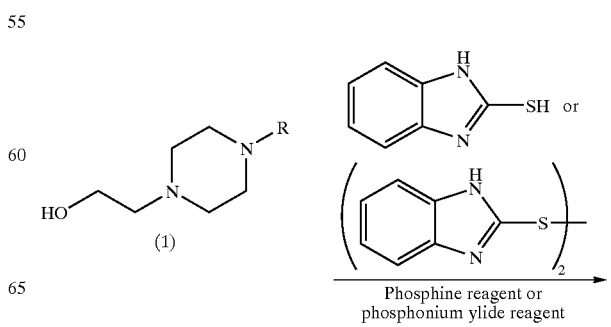

-continued

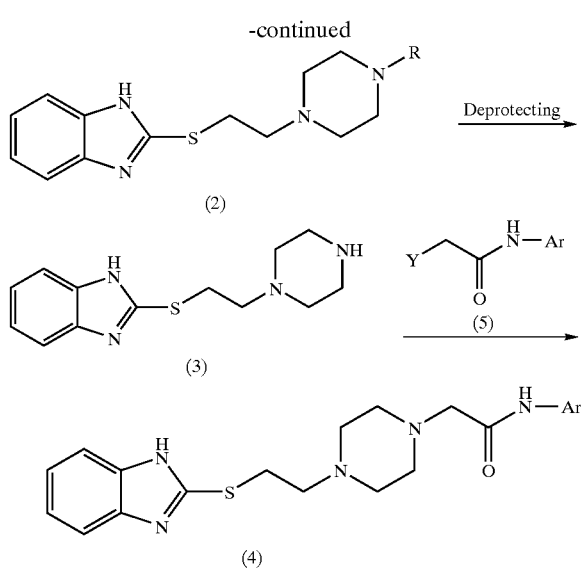

(wherein R represents a protective group and Ar represents an aryl group which may have a substituent(s)). The present invention has been accomplished on the basis of this finding.

Accordingly, the present invention provides a process for producing a compound (2), characterized in that the process comprises reacting the aforementioned compound (1) with 2-mercaptobenzimidazole or bis(2-benzimidazolyl) disulfide in the presence of a phosphine reagent or a phosphonium ylide reagent. The invention also provides a process for producing a compound (3) or a salt thereof, characterized in that the process comprises removing a protective group of the compound (2).

The present invention also provides a process for producing a cyclic diamine compound (4), characterized in that the process comprises reacting the aforementioned compound (1) with 2-mercaptobenzimidazole or bis(2-benzimidazolyl) disulfide in the presence of a phosphine reagent or a phosphonium ylide reagent, to thereby form a compound (2), removing a protective group from the compound (2), to thereby form a compound (3) or a salt thereof, and reacting a compound (5).

The present invention also provides 1-formyl-4-[2-(benzimidazol-2-ylthio)ethyl]piperazine represented by the following formula (6).

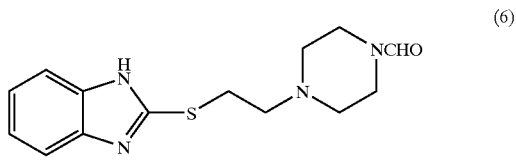

BEST MODE FOR CARRYING OUT THE INVENTION

With regard to compounds (1) and (2) of the present invention, examples of the protective group represented by "R" include amide-type protective groups such as formyl, acetyl, chloroacetyl, trichloroacetyl, trifluoroacetyl, phenylacetyl, 3-pyridylcarbonyl, benzoyl, and 4-phenylbenzoyl; urethane-type protective groups such as methoxycarbonyl, ethoxycarbonyl, benzyloxycarbonyl, 4-methoxybenzyloxycarbonyl, 2,2,2-trichloroethyloxycarbonyl, 2-trimethylsilylethyloxycarbonyl, 2-phenylethyloxycarbonyl, tert-butoxycarbonyl, vinyloxycarbonyl, allyloxycarbonyl, and 9-fluorenylmethoxycarbonyl; allyl-type protective groups such as allyl and crotyl; and benzyl-type protective groups such as benzyl and 4-methoxybenzyl. Of these, a formyl group, an acetyl group, and a tert-butoxycarbonyl group are preferred, with a formyl group being particularly preferred.

Examples of the aryl moiety of the aryl group which may have a substituent contained in compounds (4) and (5) include 6-membered aromatic hydrocarbon groups and 5 to 7 membered heterocyclic groups having as a heteroatom(s) 1 to 3 nitrogen atoms. Specific examples of preferred groups include a phenyl group, a pyridyl group, and a pyrimidyl group. Examples of the substituent include a lower alkyl group, a lower alkoxy group, a lower alkoxy-lower alkoxy group, a lower alkanoyloxy group, a lower alkoxycarbonyl-lower alkoxy group, a lower alkylsulfonyloxy group, a di-lower alkoxyphosphoryloxy group, a di-lower alkylamino group, a lower alkylthio group, a lower alkylsulfinyl group, a lower alkylsulfonyl group, a hydroxyl group, and a nitro group. The term "lower" refers to a number of carbon atoms of 1 to 6, and the alkyl moiety may be linear or branched. The following are some examples of preferred substituents. For the lower alkyl group, methyl, ethyl, n-propyl, isopropyl, and tert-butyl; for the lower alkoxy group, methoxy, ethoxy, and n-propoxy; for the lower alkoxy-lower alkoxy group, methoxymethoxy, ethoxymethoxy, and ethoxyethoxy; for the lower alkanoyloxy group, acetyloxy and propionyloxy; for the lower alkoxycarbonyl-lower alkoxy group, ethoxycarbonylmethoxy; for the lower alkylsulfonyloxy group, methylsulfonyloxy; for the di-lower alkoxyphosphoryloxy group, dimethoxyphosphoryloxyl for the di-lower alkylamino group, dimethylamino and diethylamino; for the lower alkylthio group, methylthio, ethylthio, and isopropylthio; for the lower alkylsulfinyl group, methylsulfinyl, ethylsulfinyl, and isopropylsulfinyl; and for the lower alkylsulfonyl group, methylsulfonyl, ethylsulfonyl, and isopropylsulfonyl.

Compounds (3) and (4) of the present invention may be converted to the corresponding acid-added salts. Examples of the salts include inorganic acid salts such as hydrochlorides, sulfates, nitrates, and phosphates; and organic acid salts such as methanesulfonates, maleates, fumarates, citrates, tartrates, and malates.

Compound (4) may be a non-solvated species or a hydrate or a solvated species formed from a solvent employed in production or purification such as water and alcohol.

According to the present invention, compound (2) is produced from compound (1) by use of 2-mercaptobenzimidazole or bis(2-benzimidazolyl) disulfide in the presence of a phosphine reagent or a phosphonium ylide reagent. Examples of preferred modes include [1] a method including reacting compound (1) with 2-mercaptobenzimidazole in the presence of a phosphine reagent and an azo reagent or an ethylenedicarboxylic acid reagent such as dimethyl maleate or N,N,N',N'-tetramethylfumaramide (Method A), [2] a method including reacting compound (1) with bis(2-benzimidazolyl) disulfide in the presence of a phosphine reagent (Method B), and [3] a method including reacting compound (1) with 2-mercaptobenzimidazole in the presence of a phosphonium ylide reagent (Method C).

<Method A>

In Method A, a compound (1), 2-mercaptobenzimidazole, and a phosphine reagent are dissolved in a reaction solvent, and an azo reagent or an ethylenedicarboxylic acid reagent is added to the solution. The mixture is allowed to react under an argon or nitrogen atomosphere, at 0° C. to 100° C., preferably at room temperature to 80° C., for 2 hours to 24 hours.

Examples of phosphine reagents which are useful in the reaction include trialkylphosphines such as trimethylphosphine, triethylphosphine, tripropylphosphine, triisopropylphosphine, tributylphosphine, triisobutylphosphine, and tricyclohexylphosphine; and triarylphosphines such as triphenylphosphine and diphenylphosphinopolystyrene. Of these, trimethylphosphine, tributylphosphine, and triphenylphosphine are preferred.

Examples of the azo reagent include diethyl azodicarbosylate (DEAD), 1,1'-azobis(N,N-dimethylformamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocine-2,5-dione (DHTD). Of these, diethyl azodicarbosylate is particularly preferred.

Examples of the reaction solvent include dimethylformamide, tetrahydrofuran, dioxane, acetonitrile, nitromethane, acetone, ethyl acetate, benzene, chlorobenzene, toluene, chloroform, and methylene chloride. Of these, dimethylformamide, tetrahydrofuran, dioxane, and acetonitrile are preferred, with dimethylformamide and tetrahydrofuran being particularly preferred.

<Method B>

In Method B, a compound (1), bis(2-benzimidazolyl) disulfide, and a phosphine reagent are dissolved in a solvent which is similar to those as recited in relation to method A, and the solution is allowed to react under an argon or nitrogen atmosphere, at room temperature to 100° C., preferably 60° C. to 100° C., for 2 hours to 48 hours.

The phosphine reagent employed in the reaction is trialkylphosphine or triarylphosphine as shown in Method A. Specific examples include trimethylphosphine, triethylphosphine, tripropylphosphine, triisopropylphosphine, tributylphosphine, triisobutylphosphine, tricyclohexylphosphine, triphenylphosphine, and diphenylphosphinopolystyrene. Of these, trimethylphosphine, tributylphosphine, and triphenylphosphine are preferred, with trimethylphosphine being particularly preferred.

<Method C>

In Method C, a compound (1), 2-mercaptobenzimidazole, and a phosphonium ylide reagent are dissolved in a reaction solvent, and the solution is allowed to react under an argon or nitrogen atmosphere at room temperature to 120° C., preferably 80° C. to 100° C., for 2 hours to 12 hours.

Examples of the phosphonium ylide reagent employable in the reaction include alkanoylmethylenetrialkylphosphorane, alkanoylmethylenetriarylphosphorane, alkoxycarbonylmethylenetrialkylphosphorane, alkoxycarbonylmethylenetriarylphosphorane, cyanomethylenetrialkylphosphorane, and cyanomethylenetriarylphosphorane. Examples of trialkyl include trimethyl, triethyl, tripropyl, triisopropyl, tributyl, triisobutyl, and tricyclohexyl, and examples of triaryl include triphenyl and diphenylpolystyrene.

Alternatively, the reaction may be carried out by treating a compound (1) and 2-mercaptobenzimidazole with a phosphonium halide reagent in the presence of a base, thereby forming a phosphonium ylide reagent in the reaction system.

Examples of the phosphonium halide reagent employable in the alternative method include (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (allyloxycarbonylmethyl)trialkylphosphonium halide, and (alkoxycarbonylmethyl)triarylphosphonium halide.

Notably, the aforementioned (cyanomethyl)trialkylphosphonium halide and (cyanomethyl)triarylphosphonium halide may be prepared by reacting the corresponding halogenoacetonitrile with the corresponding trialkylphosphine or triarylphosphine (Tetrahedron, vol. 57, p. 5451–5454, 2001), and alkanoylmethylenetrialkylphosphorane or a similar compound may be prepared by reacting the corresponding alkanoylhalomethyl or alkoxycarbonylhalomethyl with the corresponding trialkylphosphine or triarylphosphine in a similar manner.

Examples of trialkylphosphine and triarylphosphine employed herein include the same compounds as shown in Method A. Of these, trimethylphosphine, tributylphosphine, and triphenylphosphine are preferred, with trimethylphosphine being particularly preferred.

Examples of the aforementioned alkanoyl include formyl, acetyl, propionyl, and butyryl. Among them, acetyl, and propionyl are preferred. Examples of alkoxy in the alkoxycarbonyl include methoxy, ethoxy, propoxy, and butoxy. Of these, methoxy, ethoxy, and butoxy are preferred.

As the halogen atom, chlorine, bromine, and iodine are preferred.

Examples of the base include organic bases such as triethylamine, N,N-diisopropylethylamine, 1,4-diazabicyclo[2,2,2]octane (DABCO), 1,8-diazabicyclo[5,4,0]undec-7-ene (DBU), and 1,5-diazabicyclo[4,3,0]non-5-ene (DBN); and inorganic bases such as potassium carbonate, sodium carbonate, cesium carbonate, lithium carbonate, lithium diisopropylamide, and potassium hexamethyldisilazide. Of these, N,N-diisopropylethylamine, potassium carbonate, lithium diisopropylamide, and potassium hexamethyldisilazide are preferred, with N,N-diisopropylethylamine and potassium carbonate being particularly preferred.

Examples of preferred reaction solvents include dioxane, tetrahydrofuran, toluene, benzene, dimethylformamide, dimethyl sulfoxide, acetonitrile, and propionitrile. Among them, propionitrile is particularly preferred.

By removing the protective group of the thus-produced compound (2), 1-[2-(benzimidazol-2-ylthio)ethyl]piperazine (compound (3)) or a salt thereof can be produced.

Deprotection reaction may be performed through any known deprotection reaction (e.g., hydrolysis under acidic conditions by use of hydrochloric acid or a similar acid, hydrolysis in the presence of an alkali such as sodium hydroxide, hydrogenolysis, or reduction).

For example, an amide-type protective group can be removed by use of an acid such as hydrochloric acid, phosphoric acid, sulfuric acid, or trifluoroacetic acid or an alkali such as sodium hydroxide or potassium hydroxide, in a solvent such as methanol, ethanol, propanol, tetrahydrofuran, or dioxane or in a mixture of water and any of the aforementioned solvent generally at 0 to 100° C. A urethane-type protective group can be removed by use of an acid such as hydrochloric acid, phosphoric acid, sulfuric acid, or trifluoroacetic acid or a reducing agent such as hydrogen-palladium, zinc, or sodium borohydride, in a solvent such as methanol, ethanol, propanol, tetrahydrofuran, dioxane, acetonitrile, or ethyl acetate generally at 0 to 100° C. An allyl-type protective group can be removed by treating the compound with a complex such as a zirconium complex, a ruthenium complex, a palladium complex, or an iridium complex, thereby isomerizing a vinyl group to the corresponding enamine form, followed by hydrolysis. A benzyl-type protective group can be removed through hydrolysis in a solvent (e.g.; methanol or ethanol) in the presence of a catalyst (e.g.; palladium or platinum).

A cyclic diamine compound (4) or a salt thereof can be produced by reacting a compound (3) or a salt thereof with a halogenoacetamide compound (5).

The reaction may be performed through a known alkylation procedure. Specifically, the reaction may be performed in a solvent such as methanol, ethanol, propanol, tetrahydrofuran, dioxane, acetone, acetonitrile, dimethylformamide, or dimethyl sulfoxide or in a mixture of water and any of the aforementioned solvent in the presence of a base generally at 0 to 100° C.

Examples of the base employed in the alkylation include inorganic bases such as alkali metal hydroxides (e.g., sodium hydroxide and potassium hydroxide); alkali metal carbonates (e.g., sodium carbonate, potassium carbonate, and cesium carbonate); and alkali metal hydrogencarbonates (e.g., sodium hydrogencarbonate and potassium hydrogencarbonate); and organic bases such as pyridine, triethylamine, N,N-diisopropylethylamine, N-methylmorpholine, N,N-dimethylaniline, DABCO, DBU, and DBN.

The halogen atom represented by Y is preferably a chlorine atom, a bromine atom, or an iodine atom. Of these, a bromine atom is particularly preferred.

Alternatively, compound (1) may be yielded through a known protective group introducing reaction (see "PROTECTIVE GROUPS IN ORGANIC SYNTHESIS 2nd Ed," authored by THEODORA W. GREENE, PETER G. N. WUTS, JOHN WILEY SONS, INC). Specifically, compound (1) is produced by reacting a protective group-introducing reagent for R with 1-(2-hydroxyethyl)piperazine in the presence or absence of a base.

Examples of the amide-type protective group-introducing reagent include the corresponding acyl halides, carboxylic anhydrides, carboxylates, and carboxylate active esters. Examples of the urethane-type protective group-introducing reagent include halogenated alkyl carbonates, halogenated aryl carbonates, halogenated aralkyl carbonates, active alkyl carbonates, active aryl carbonates, active aralkyl carbonates, and tert-butyl bicarbonate. Examples of the allyl-type protective group-introducing reagent include the corresponding halogenated aryl derivatives, and examples of the benzyl-type protective group-introducing reagent include the corresponding halogenated benzyl derivatives.

EXAMPLES

The present invention will next be described in more detail by way of examples.

Example 1

Production of 1-formyl-4-[2-(benzimidazol-2-ylthio)ethyl]piperazine

To a solution containing 1-formyl-4-(2-hydroxyethyl)piperazine (1.58 g, 10 mmol), 2-mercaptobenzimidazole (5.56 g, 37 mmol), and triphenylphosphine (9.26 g, 35.3 mmol) in dimethylformamide (100 mL), diethyl azodicarboxylate (5.19 g, 29.8 mmol) was added dropwise over 5 minutes with ice-cooling and stirring under argon. The mixture was stirred for 80 minutes at room temperature, and then water (2 mL) was added to the mixture so as to deactivate the reagent. The reaction mixture was concentrated under reduced pressure, and chloroform (200 mL) was added to the residue. Insoluble material was removed through filtration, and the filtrate was concentrated under reduced pressure. 2N Hydrochloric acid (20 mL) and ethyl acetate (100 mL) were added to the residue, and the liquid was partitioned. The organic layer was extracted with 2N hydrochloric acid (20 mL×2). The aqueous extract and the aqueous layer were combined, and the mixture was washed with chloroform (50 mL×2). The pH of the mixture was adjusted to about 9 through addition of potassium carbonate, followed by extraction with chloroform (50 mL×3), washing the organic layer with saturated brine, drying over sodium sulfate anhydrate, and removing the solvent. The thus-formed crude product was crystallized from acetone-diethyl ether, thereby yielding 2.19 g of 1-formyl-4-[2-(benzimidazol-2-ylthio)ethyl]piperazine (yield: 76%) as a colorless crystalline powder. The crystallization mother liquor was concentrated under reduced pressure, and the residue was purified through silica gel column chromatography (eluent: chloroform: methanol=50:1 to 20:1), thereby yielding 0.42 g of 1-formyl-4-[2-(benzimidazol-2-ylthio)ethyl]piperazine (yield: 14%) as a colorless crystalline powder. The overall yield was 90%.

Melting point: 146–148° C. IR (KBr) cm$^{-1}$: 3440, 3049, 1619, 1441, 742.

$^1$H-NMR (CDCl$_3$) δ: 2.59 (2H, t, J=5.3 Hz), 2.63 (2H, t, J=5.3 Hz), 2.91 (2H, t, J=6.1 Hz), 3.37 (2H, t, J=6.1 Hz), 3.46 (2H, t, J=5.0 Hz), 3.65 (2H, t, J=5.0 Hz), 7.18 (1H, dd, J=7.3, 3.0 Hz), 7.21 (1H, dd, J=7.3, 3.0 Hz), 7.41–7.58 (2H, m), 8.06 (1H, s). MS (m/z): 290 (M$^+$, 3.2), 140 (100).

Element analysis (as C$_{14}$H$_{18}$N$_4$OS) Calculated: C, 57.91; H, 6.25; N, 19.29; S, 11.04. Found: C, 57.78; H, 6.30; N, 19.12; S, 11.15.

Example 2

Production of 1-formyl-4-[2-(benzimidazol-2-ylthio)ethyl]piperazine

To a solution containing 1-formyl-4-(2-hydroxyethyl)piperazine (1.90 g, 12 mmol), 2-mercaptobenzimidazole (1.50 g, 10 mmol), and N,N-diisopropylethylamine (1.80 g, 14 mmol) in propionitrile (16 mL), cyanomethyltrimethylphosphonium iodide (2.80 g, 11.5 mmol) was added under argon, and the mixture was refluxed for 2 hours. After cooling, the reaction mixture was poured into water (100 mL), and the liquid was subjected to extraction with chloroform (100 mL×3). The organic layer was washed with saturated brine, followed by drying over sodium sulfate anhydrate and removing the solvent through filtration. The thus-formed crude product was crystallized from acetone-diethyl ether, thereby yielding 2.50 g of 1-formyl-4-[2-(benzimidazol-2-ylthio)ethyl]piperazine (yield: 86%) as a colorless crystalline powder.

Example 3

Production of 1-formyl-4-[2-(benzimidazol-2-ylthio)ethyl]piperazine

The procedure of Example 2 (reaction, treatment, and purification through silica gel column chromatography) was repeated, except that potassium carbonate was used instead of N,N-diisopropylethylamine, to thereby yield 1-formyl-4-[2-(benzimidazol-2-ylthio)ethyl]piperazine (yield: 81%).

Example 4

Production of 1-formyl-4-[2-(benzimidazol-2-ylthio)ethyl]piperazine

To a solution containing 1-formyl-4-(2-hydroxyethyl)piperazine (1.42 g, 9.0 mmol) and bis(2-benzimidazolyl) disulfide (8.06 g, 27 mmol) in anhydrous pyridine (15 mL), tributylphosphine (5.46 g, 27 mmol) was added dropwise under argon, and then the mixture was stirred for 12 hours at room temperature. The reaction mixture was concentrated under reduced pressure, and chloroform (100 mL) was added to the residue. Insoluble matter was removed through filtration, and the filtrate was concentrated. Subsequently, 2N hydrochloric acid (100 mL) and ethyl acetate (100 mL) were added to the residue, and the organic layer was partitioned. The organic layer was extracted with 2N hydrochloric acid (50 mL) and water (50 mL). The extract and the aqueous layer were combined, and the mixture was washed with ethyl acetate (50 mL×2). The pH of the mixture was adjusted to about 10 through addition of sodium carbonate to the washed aqueous layer, followed by extraction with chloroform (100 mL, 50 mL×2), washing the organic layer with saturated brine, drying over sodium sulfate anhydrate, removing the solvent. The thus-formed crude product was crystallized from acetone-diethyl ether, thereby yielding 1.50 g of 1-formyl-4-[2-(benzimidazol-2-ylthio)ethyl]piperazine (yield: 57%) as a colorless crystalline powder.

Example 5

Production of 1-[2-(benzimidazol-2-ylthio)ethyl]piperazine trihydrochloride

1-Formyl-4-[2-(benzimidazol-2-ylthio)ethyl]piperazine (1.45 g, 5.0 mmol) was dissolved in methanol (20 mL). 12N Hydrochloric acid (2 mL) was added to the solution, and the mixture was stirred for 18 hours at room temperature. The reaction mixture was concentrated under reduced pressure, and the thus-formed solid material was crystallized from chloroform-methanol, to thereby yield 1.67 g of 1-[2-(benzimidazol-2-ylthio)ethyl]piperazine trihydrochloride (yield: 90%) as a colorless crystalline powder.

Melting point: 241–246° C. IR (KBr) cm$^{-1}$: 3374, 2938, 2647, 1630, 1522.

$^1$H-NMR (CDCl$_3$)δ: 3.37–3.50 (4H, m), 3.43–3.57 (4H, m), 3.54 (2H, t, J=7.0 Hz), 3.81 (2H, t, J=7.0 Hz), 7.31 (2H, dd, J=5.9, 3.3 Hz), 7.59 (2H, dd, J=5.9, 3.3 Hz), 9.73 (2H, br s). MS (m/z): 262 (M$^+$–3HCl, 3.1), 140 (100).

Element analysis (C$_{13}$H$_{18}$N$_4$S.3HCl) Calculated: C, 42.00; H, 5.69; N, 15.07. Found: C, 41.87; H, 5.62; N, 14.98.

Example 6

Production of 2-[4-[2-(benzimidazol-2-ylthio)ethyl]piperazin-1-yl]-N-[2,4-bis(methylthio)-6-methylpyridin-3-yl]acetamide 1-[2-(Benzimidazol-2-ylthio)ethyl]piperazine trihydrochloride 1.0 g (2.69 mmol) was suspended in acetonitrile (30 mL), and potassium carbonate 1.45 g (10.49 mmol) was added to the suspension. Water (8 mL) was added dropwise to the mixture under stirring at room temperature until the entirety of the suspension assumed a homogeneous solution. Subsequently, N-[2,4-bis(methylthio)-6-methylpyridin-3-yl]-2-bromoacetamide 810 mg (2.52 mmol) was gradually added to the mixture, and the mixture was stirred for 2.5 hours at room temperature. The reaction mixture was diluted with water (50 mL) and extracted with chloroform (100 mL×3). The organic layer was washed with saturated brine (50 mL), followed by drying over sodium sulfate anhydrate and concentrating under reduced pressure. The residue was purified through silica gel column chromatography (eluent: chloroform:saturated ammonia in methanol=20:1). The thus-obtained oily product was crystallized from ethanol-diethyl ether, thereby yielding 1.16 g of 2-[4-[2-(benzimidazol-2-ylthio)ethyl] piperazin-1-yl]-N-[2,4-bis(methylthio)-6-methylpyridin-3-yl]acetamide (yield: 88%) as a colorless crystalline powder.

Melting point: 96–97° C. IR (KBr) cm$^{-1}$: 3273, 1672, 1564, 1534, 1488.

$^1$H-NMR (CDCl$_3$)δ: 2.42 (3H, s), 2.50 (3H, s), 2.53 (3H, s), 2.71–3.05 (10H, m), 3.23 (2H, t, J=5.4 Hz), 3.35 (2H, s), 6.68 (1H, s), 7.18–7.23 (2H, m), 7.35–7.75 (2H, m), 8.43 (1H, br.s), 12.80 (1H, br.s). MS (m/z): 502 (M$^+$)

Element analysis as (C$_{23}$H$_{30}$N$_6$OS$_3$.1.2H$_2$O) Calculated: C, 52.68; H, 6.23; N, 16.03. Found: C, 52.63; H, 5.96; N, 15.82.

Example 7

Production of 2-[4-[2-(benzimidazol-2-ylthio)ethyl]piperazin-1-yl]-N-(2,4,6-triisopropylphenyl)acetamide The procedure of Example 6 (reaction and treatment) was repeated, except that N-(2,4,6-triisopropylphenyl)-2-bromoacetamide was used instead of N-[2,4-bis(methylthio)-6-methylpyridin-3-yl]-2-bromoacetamide, to thereby yield 2-[4-[2-(benzimidazol-2-ylthio)ethyl]piperazin-1-yl]-N-(2, 4,6-triisopropylphenyl)acetamide.

Example 8

Production of 2-[4-[2-(benzimidazol-2-ylthio)ethyl]piperazin-1-yl]-N-[2,4-bis(isopropylthio)-6-methylpyridin-3-yl]acetamide The procedure of Example 6 (reaction and treatment) was repeated, except that N-[2,4-bis(isopropylthio)-6-methylpyridin-3-yl]-2-bromoacetamide was used instead of N-[2,4-bis(methylthio)-6-methylpyridin-3-yl]-2-bromoacetamide, to thereby yield 2-[4-[2-(benzimidazol-2-ylthio)ethyl]piperazin-1-yl]-N-[2,4-bis(isopropylthio)-6-methylpyridin-3-yl]acetamide.

Industrial Applicability

According to the present invention, cyclic diamine compounds (4) useful as drugs or salts or intermediates thereof can be produced at high levels of yield and purity in terms of industrially advantageous productivity.

The invention claimed is:

1. A process for producing a compound represented by the following formula (2):

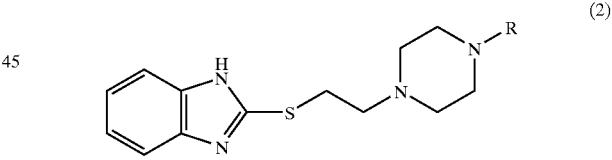

(wherein R represents a protective group), characterized in that the process comprises reacting a compound represented by the following formula (1):

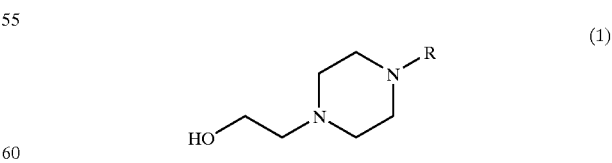

(wherein R represents the same as mentioned above) with 2-mercaptobenzimidazole or bis(2-benzimidazolyl) disulfide in the presence of a phosphine reagent or a phosphonium ylide reagent.

2. A process for producing 1-[2-(benzimidazol-2-ylthio) ethyl]piperazine represented by the following formula (3):

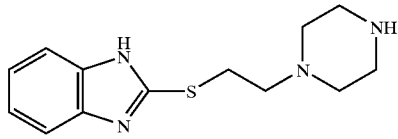

or a salt thereof, characterized in that the process comprises reacting a compound represented by the following formula (1):

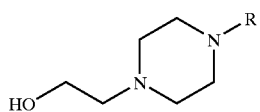

(wherein R represents a protective group) with 2-mercaptobenzimidazole or bis(2-benzimidazolyl) disulfide in the presence of a phosphine reagent or a phosphonium ylide reagent, to thereby form a compound represented by the following formula (2):

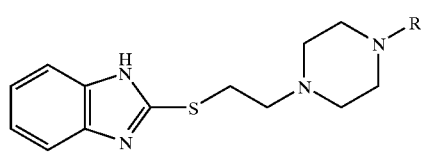

(wherein R represents the same as mentioned above), and subsequently, removing the protective group.

3. A process for producing cyclic diamine compound represented by the following formula (4):

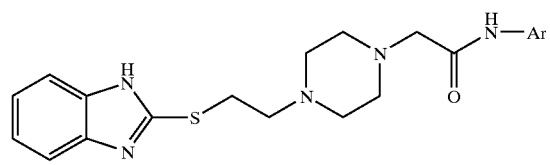

(wherein Ar represents an optionally substituted aryl group) or a salt thereof, characterized in that the process comprises reacting a compound represented by the following formula (1):

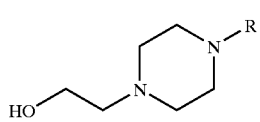

(wherein R represents a protective group) with 2-mercaptobenzimidazole or bis(2-benzimidazolyl) disulfide in the presence of a phosphine reagent or a phosphonium ylide reagent, to thereby form a compound represented by the following formula (2):

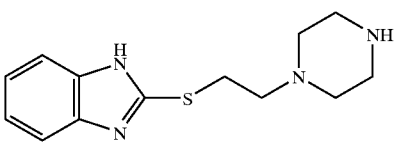

(wherein R represents the same as mentioned above), subsequently, removing the protective group, to thereby form 1-[2-(benzimidazol-2-ylthio)ethyl]piperazine represented by the following formula (3):

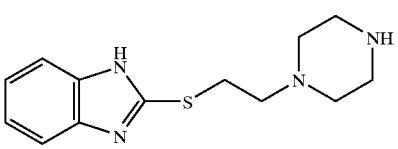

or a salt thereof, and reacting the compound or a salt with a halogenoacetamide compound represented by the following formula (5):

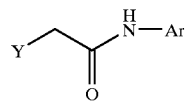

(wherein the Ar represents the same as mentioned above and Y represents a halogen atom).

4. The process as described in any one of claims 1 to 3, wherein the compound represented by formula (1) has been produced by reacting 4-(2-hydroxyethyl)piperazine with a reagent for introducing protective group to an amino group.

5. The process as described in any one of claims 1 to 4, wherein R is a formyl group.

6. 1-Formyl-4-[2-(benzimidazol-2-ylthio)ethyl]piperazine represented by the following formula (6).

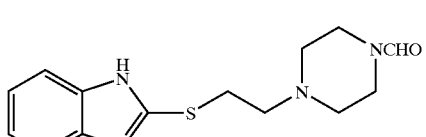

* * * * *

UNITED STATES PATENT AND TRADEMARK OFFICE
CERTIFICATE OF CORRECTION

PATENT NO. : 6,998,486 B2
APPLICATION NO. : 10/498984
DATED : February 14, 2006
INVENTOR(S) : Kimiyuki Shibuya et al.

It is certified that error appears in the above-identified patent and that said Letters Patent is hereby corrected as shown below:

Claim 3, column 12, lines 6-15 should read as follows:

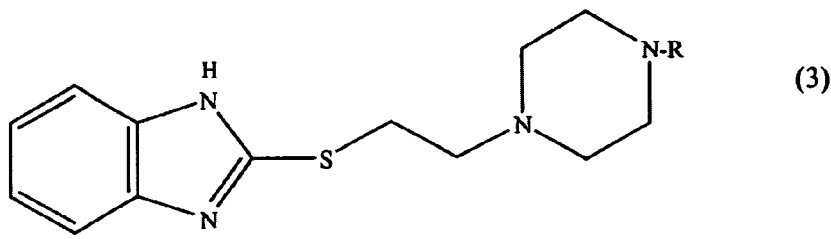  (3)

Signed and Sealed this

Tenth Day of October, 2006

JON W. DUDAS
*Director of the United States Patent and Trademark Office*